United States Patent [19]
Kehne et al.

[11] Patent Number: 5,663,118
[45] Date of Patent: Sep. 2, 1997

[54] FLUOROMETHYLSULFONYL-SUBSTITUTED PYRIDYLSULFONYLUREAS AS HERBICIDES, PROCESS FOR THEIR PREPARATION, AND THEIR USE

[75] Inventors: Heinz Kehne; Lothar Willms, both of Hofheim; Klaus Bauer, Hanau; Hermann Bieringer, Eppstein, all of Germany

[73] Assignee: Hoechst Schering AgrEvo GmbH, Berlin, Germany

[21] Appl. No.: 224,324

[22] Filed: Apr. 7, 1994

Related U.S. Application Data

[63] Continuation-in-part of Ser. No. 859,513, Jun. 8, 1992.

[30] Foreign Application Priority Data

Apr. 9, 1993 [DE] Germany ............ 43 11 787.2

[51] Int. Cl.$^6$ .................. C07D 401/12; A01N 43/54
[52] U.S. Cl. ................ 504/215; 544/320; 544/331
[58] Field of Search ............. 504/215; 544/320, 544/331

[56] References Cited

U.S. PATENT DOCUMENTS

| | | | |
|---|---|---|---|
| 4,356,135 | 10/1982 | Francois et al. | 264/61 |
| 4,480,101 | 10/1984 | Meyer | 544/320 |
| 4,744,814 | 5/1988 | Kimura et al. | 544/320 |
| 4,786,734 | 11/1988 | Hanagan et al. | 544/320 |
| 4,838,926 | 6/1989 | Hanagan et al. | 544/320 |
| 5,139,565 | 8/1992 | Kimura et al. | 544/320 |
| 5,235,050 | 8/1993 | Kehne | 544/63 |

FOREIGN PATENT DOCUMENTS

| | | |
|---|---|---|
| 589250 | 8/1987 | Australia . |
| 2073446 | 7/1991 | Canada . |
| 0004808 | 10/1979 | European Pat. Off. . |
| 0070804 | 1/1983 | European Pat. Off. . |
| 0184385 | 6/1986 | European Pat. Off. . |
| 0232067 | 8/1987 | European Pat. Off. . |
| 0237292 | 9/1987 | European Pat. Off. . |
| 0272855 | 6/1988 | European Pat. Off. . |
| 0451468 | 10/1991 | European Pat. Off. . |
| 0508348 | 10/1992 | European Pat. Off. . |
| 82/5671 | 3/1982 | South Africa . |
| 82/5045 | 7/1982 | South Africa . |
| 87/0436 | 1/1987 | South Africa . |
| WO91/10660 | 7/1991 | WIPO . |

OTHER PUBLICATIONS

Chemische Berichte, Lange et al., "Improved Synthesis of Fluoromethane Sulfonyl Chloride", 1991. pp. 1879–1880.
Research Disclosure, Mar. 1987, 27556, p. 162.

*Primary Examiner*—John M. Ford
*Attorney, Agent, or Firm*—Curtis Morris & Safford P C

[57] ABSTRACT

Fluoromethylsulfonyl-substituted pyridylsulfonylureas as herbicides, process for their preparation, and their use.

Compounds of the formula (II) or salts thereof, (II)

$R^1$ is hydrogen, methyl or ethyl,

Z is CH or N and one of the radicals X and Y is halogen, $(C_1-C_2)$alkyl, $(C_1-C_2)$alkoxy, $OCHF_2$ or $CF_3$ and the other one of the radicals X and Y is $(C_1-C_2)$alkyl, $(C_1-C_2)$alkoxy or $OCHF_2$, are suitable as selective herbicides for use in crops.

They can be prepared by the process as claimed in claim 4, in which, in some cases, intermediates of the formula (III) are employed:

(III)

8 Claims, No Drawings

FLUOROMETHYLSULFONYL-SUBSTITUTED PYRIDYLSULFONYLUREAS AS HERBICIDES, PROCESS FOR THEIR PREPARATION, AND THEIR USE

RELATED APPLICATIONS

This application is a continuation-in-part of application Ser. No. 07/859,513, filed Jun. 8, 1992.

The patent application WO 91/10660 and EP-A-451468 apply, inter alia, to pyridylsulfonylureas of the formula (I),

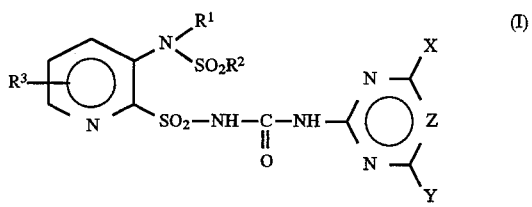

in which $R^1$ is hydrogen or optionally substituted alkyl, alkenyl, alkynyl, alkoxy, alkylcarbonyl, alkylsulfonyl or phenylsulfonyl and $R^2$ is alkyl, haloalkyl, specifically $CF_3$, alkoxyalkyl, alkenyl, dialkylamino or optionally substituted phenyl, $R^3$ is hydrogen, halogen or optionally substituted alkyl, alkoxy, alkylthio, aminosulfonyl or aminocarbonyl or alkylamino, dialkylamino or alkoxycarbonyl, X, Y independently of one another are halogen, alkyl, haloalkyl, alkoxy or haloalkoxy and Z is CH or N.

Surprisingly, it has now been found that certain compounds of the above type in which $R^2$ is the $-CH_2F$ group, show a superior activity or better crop plant tolerance in comparison with compounds which have a similar structure, for example those in which $R^2$ is $CF_3$ or other haloalkyl groups.

The present invention therefore relates to compounds of the formula (II) or salts thereof

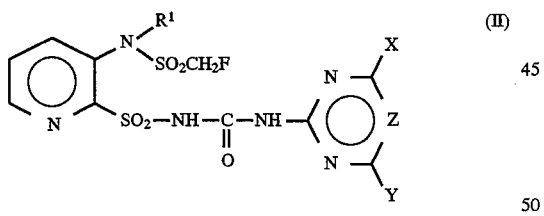

in which $R^1$ is hydrogen, methyl or ethyl,

Z is CH or N and one of the radicals X and Y is halogen, $(C_1-C_2)$alkyl, $(C_1-C_2)$alkoxy, $OCHF_2$ or $CF_3$ and the other one of the radicals X and Y is $(C_1-C_2)$alkyl, $(C_1-C_2)$alkoxy or $OCHF_2$.

Preferred compounds of the formula (II) or salts thereof are those in which Z is CH and those in which $R^1$ is methyl or ethyl in particular methyl.

Other preferred compounds of the formula (II), according to the invention are those in which X and Y independently of one another are methoxy, ethoxy, difluoromethoxy or methyl.

The present invention furthermore relates to processes for the preparation of the compounds of the formula (II) or salts thereof, which comprise (a) reacting compounds of the formula (III)

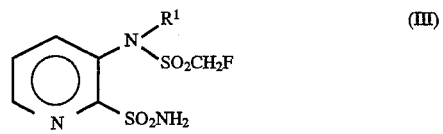

with a heterocyclic carbamate of the formula (IV)

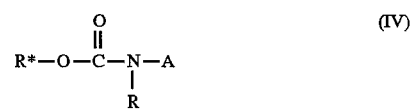

in which $R^*$ is phenyl or $(C_1-C_4)$alkyl, or (b) reacting pyridylsulfonylcarbamates of the formula (V)

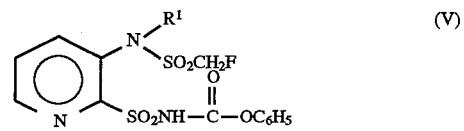

with an amino heterocycle of the formula (VI)

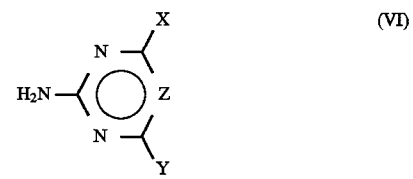

or (c) reacting a sulfonyl isocyanate of the formula (VII)

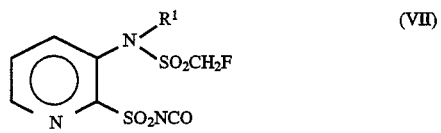

with an amino heterocycle of the formula (VI) or (d) in a one-pot reaction, first reacting an amino heterocycle of the formula (VI) with phosgene in the presence of a base, such as, for example, triethylamine, and reacting the resulting intermediate form with a pyridinesulfonamide of the formula (III) (for example analogously to EP-A-232 067) or (e) reacting a zwitterionic bicyclic structure of the formula (VIII)

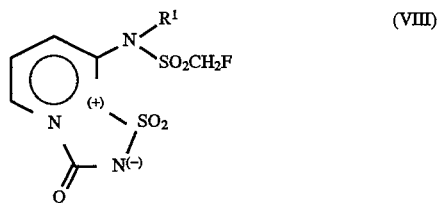

with an amino heterocycle of the formula (VI) (analogously to EP-A-508348).

The compounds of the formula (III) and (VI) are preferably reacted with base catalysis in an inert organic solvent, such as, for example, dichloromethane, acetonitrile, dioxane or THF, at temperatures between 0° C. and the boiling point of the solvent. The base used is preferably 1,8-diazabicyclo [5.4.0]undec-7-ene (DBU) or trimethylaluminum or triethylaluminum.

The sulfonamides (III) are novel compounds. They, and their preparation, are also a subject of this invention. They are obtained starting from a 3-amino-2-halopyridine, for example 3-amino-2-chloropyridine, which is first sulfonated using fluoromethanesulfonyl chloride, accessible by the method of U. Lange and A. Senning, Chem. Ber. 124, 1879 (1991). It may then be desired to carry out an alkylation (see $R^1$) and the product is then reacted with S-nucleophiles, such as, for example, benzylmercaptan or thiourea. The compounds formed in this manner are converted into the sulfonyl chlorides using sodium hypochlorite or chlorine (analogously to EP-A-272 855), and these sulfonyl chlorides are then reacted either directly with ammonia or with tert-butylamine via the tert-butylamides, followed by elimination of protective groups, to give the sulfonamides of the formula (III).

Alternatively, the sulfonamides (III) are obtained starting from a suitable 3-amino-2-alkylmercaptopyridine by N-sulfonation using fluoromethanesulfonyl chloride, if appropriate N-alkylation (depending on $R^1$) and chlorination with chlorine or sodium hypochlorite to give the corresponding sulfonyl chloride which is then reacted either directly with ammonia or with tert-butylamine, followed by elimination of protective groups to give (III).

The carbamates of the formula (IV) can be prepared by methods which are described in the South African Patent Applications 82/5671 and 82/5045 or in EP-A-70804 (U.S. Pat. No. 4,480,101) or RD 275056.

The reaction of the compounds (V) with the amino heterocycles (VI) is preferably carried out in inert, aprotic solvents, such as, for example, dioxane, acetonitrile or tetrahydrofuran, at temperatures between 0° C. and the boiling point of the solvent. The starting materials (VI) required are known from the literature or can be prepared by processes known from the literature. The pyridylsulfonyl-carbamates of the formula (V) are obtained analogously to EP-A-4 808 or EP-A-237 292.

The pyridylsulfonyl isocyanates of the formula (VII) can be prepared analogously to EP-A-184 385 and reacted with the amino heterocycles (VI).

The "inert solvents" mentioned in the above process variants are in each case solvents which are inert under the reaction conditions in question but which do not have to be inert under any reaction conditions.

The compounds of the formula (II) can form salts in which the hydrogen of the —$SO_2$—NH group is replaced by a cation which is suitable for agriculture. Examples of these salts are metal salts, in particular alkali metal salts or alkaline earth metal salts, in particular sodium salts and potassium salts, or else ammonium salts, or salts with organic amines. Other salts which are suitable are addition salts with acids.

The salts of the compounds of the formula (II) are preferably prepared in inert solvents, such as, for example, water, methanol or acetone, at temperatures of 0° C.–100° C. Bases which are suitable for the preparation of the salts according to the invention are, for example, alkali metal carbonates, such as potassium carbonate, alkali metal hydroxides and alkaline earth metal hydroxides, ammonia or ethanolamines. Acids which are particularly suitable for salt formation are HCl, HBr, $H_2SO_4$ and $HNO_3$.

The general explanations of the invention which follow apply not only to the compounds of the formula (II) but also to the salts thereof.

The compounds of the formula (II) according to the invention have an excellent herbicidal activity against a broad range of economically important monocotyledon and dicotyledon harmful plants. The active substances also act efficiently on perennial weeds which produce shoots from rhizomes, rootstocks or other perennial organs and which are difficult to control. In this context, it does not matter whether the substances are applied before sowing, pre-emergence or post-emergence. Specifically, examples may be mentioned of some representatives of the monocotyledon and dicotyledon weed flora which can be controlled by the compounds according to the invention, without the enumeration being a restriction to certain species.

Examples of weed species on which the active substance acts efficiently are, from amongst the monocotyledons, Avena, Lolium, Alopecurus, Phalaris, Echinochloa, Digitaria, Setaria and also Cyperus species from the annual sector and from amongst the perennial species Agropyron, Cynodon, Imperata and Sorghum, and also perennial Cyperus species.

In the case of the dicotyledon weed species, the range of action extends to species such as, for example, Galium, Viola, Veronica, Lamium, Stellaria, Amaranthus, Sinapis, Ipomoea, Matricaria, Abutilon and Sida from amongst the annuals, and Convolvulus, Cirsium, Rumex and Artemisia in the case of the perennial weeds.

The active substances according to the invention equally effect outstanding control of weeds which occur under the specific conditions of rice growing, such as, for example, Sagittaria, Alisma, Eleocharis, Scirpus and Carperus.

If the compounds according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

If the active substances are applied post-emergence on the green parts of the plants, growth equally stops drastically a very short time after the treatment and the weed plants remain at the growth stage of the point of time of application, or they die completely after a certain time, so that in this manner competition by the weeds, which is harmful to the crop plants, is eliminated at a very early point in time and in a sustained manner.

Even though the compounds according to the invention have an excellent herbicidal activity against monocotyledon and dicotyledon weeds, crop plants of economically important crops, such as, for example, wheat, barley, rye, rice, maize, sugar beet, cotton and soya, are damaged not at all, or only to a negligible extent. For these reasons, the present compounds are highly suitable for selectively controlling undesired plant growth in plantings for agricultural use.

Moreover, the substances according to the invention have outstanding growth-regulatory properties in crop plants. They engage in the plant metabolism in a regulating manner and can therefore be used for influencing plant constituents in a targeted manner and for facilitating harvesting, such as, for example, by provoking dessication and stunted growth. Moreover, they are also suitable for generally controlling and inhibiting undesired vegetative growth without destroying the plants in the process. Inhibition of the vegetative growth plays an important role in a large number of monocotyledon and dicotyledon crops since it allows lodging to be reduced or prevented completely.

The compounds according to the invention can be used in the conventional preparations as wettable powders, emulsifiable concentrates, sprayable solutions, dusts or granules. The invention therefore also relates to herbicidal and plant-growth regulating compositions which contain the compounds of the formula (II) or salts thereof.

The compounds of the formula (II) can be formulated in various ways, depending on the prevailing biological and/or chemical-physical parameters. The following are, for example, suitable possibilities for formulation: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing agents, granules for broadcasting and soil application, granules (GR) in the form of microgranules, spray granules, coated granules, adsorption granules, water-dispersible granules (WG), water-soluble granules (SG), ULV formulations, microcapsules and waxes.

These abovementioned formulation types are known in principle and are described, for example, Winnacker-Küchler, "Chemische Technologie [Chemical Technology]", Volume 7, C. Hauser Verlag Munich, 4th Ed., 1986; Wade van Valkenburg, "Pesticides Formulations", Marcel Dekker, New York, 1973; K. Martens, "Spray Drying Handbook", 3rd Ed., 1979, G. Goodwin Ltd. London.

The formulation auxiliaries required, such as inert materials, surfactants, solvents and other additives, are likewise known and are described, for example, in: Watkins, "Handbook of Insecticide Dust Diluents and Carriers", 2nd Ed., Darland Books, Caldwell N.J., H. V. Olphen, "Introduction to Clay Colloid Chemistry", 2nd Ed., J. Wiley & Sons, New York; C. Marsden, "Solvents Guide", 2nd Ed., Interscience, New York, 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., New York, 1964; Schönfeldt, "Grenzflächenaktive Äthylenoxidaddukte [Surface-active Ethylene Oxide Adducts]", Wiss. Verlagsgesell., Stuttgart 1976; Winnacker-Küchler, "Chemische Technologie [Chemical Technology]", Volume 7, C. Hauser Verlag Munich, 4th Ed., 1986.

Combinations with other pesticidally active substances, such as, for example, insecticides, acaricides, herbicides, fungicides, safenets, fertilizers and/or growth regulators may also be prepared on the basis of these formulations, for example in the form of a readymix or as a tank mix.

Wettable powders are preparations which are uniformly dispersible in water and which, besides the active substance, also contain ionic and/or non-ionic surfactants (wetting agents, dispersants) for example polyoxethylated alkylphenols, polyoxethylated fatty alcohols, polyoxethylated fatty amines, fatty alcohol polyglycol ether sulfates, alkanesulfonates or alkylbenzenesulfonates, sodium ligninsulfonate, sodium 2,2'-dinaphthylmethane-6,6'-disulfonate, sodium dibutylnaphthalenesulfonate, or alternatively sodium oleoylmethyltaurinate, in addition to a diluent or inert substance. To prepare the wettable powders, the herbicidal active substances are, for example, finely ground in conventional apparatus, such as hammer mills, blower mills and air-jet mills, and simultaneously or subsequently mixed with the formulation auxiliaries.

Emulsifiable concentrates are prepared by dissolving the active substance in an organic solvent, for example butanol, cyclohexanone, dimethylformamide, xylene and also higher-boiling aromatic compounds or hydrocarbons or mixtures of organic solvents, with the addition of one or more ionic and/or non-ionic surfactants (emulsifiers). Examples of emulsifiers which can be used are: calcium salts of an alkylarylsulfonic acid, such as calcium dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, alkyl polyethers, sorbitan esters, such as sorbitan fatty acid esters or polyoxyethylene sorbitan esters, such as polyoxyethylene sorbitan fatty acid esters.

Dusts are obtained by grinding the active substance with finely divided solid substances, for example talc or natural clays, such as kaolin, bentonits, pyrophyllite or diatomaceous earth.

Suspension concentrates can be water- or oil-based. They can be prepared, for example, by wet grinding by means of commercially available bead mills, if appropriate with the addition of surfactants as already mentioned, for example, above in the case of the other formulation types.

Emulsions, for example oil-in-water emulsions (EW) can be prepared, for example, by means of stirrers, colloid mills and/or static mixers using aqueous organic solvents and, if appropriate, surfactants as already mentioned, for example, above in the case of the other formulation types.

Granules can be produced either by spraying the active substance onto adsorptive, granulated inert material or by applying active substance concentrates onto the surface of carriers, such as sand, kaolinires or granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

As a rule, water-dispersible granules are prepared by the customary processes, such as spray-drying, fluidized-bed granulation, disk granulation, mixing by means of high-speed stirrers and extrusion without solid inert material.

To prepare disk, fluidized-bed, extruder and spray granules, see, for example, processes in "Spray-Drying Handbook" 3rd Ed., 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57.

For more detailed information on the formulation of crop protection products, see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As rule, the agrochemical preparations contain 0.1 to 99% by weight, in particular 0.1 to 95% by weight, of active substance of the formula (II).

The concentration of active substance in wettable powders is, for example, about 10 to 90% by weight; the remainder to 100% by weight is composed of conventional formulation components. In the case of emulsifiable concentrates, the concentration of active substance can be about 1, to 90, preferably 5 to 80% by weight. Formulations in the form of dusts usually contain 1 to 30, preferably 5 to 20% by weight of active substance, sprayable solutions about 0.05 to 80, preferably 2 to 50% by weight. In the case of water-dispersible granules, the active substance content depends partly on whether the active compound is liquid or solid and on which granulation auxiliaries, fillers etc. are used. For example, the active substance content in the case of the water-dispersible granules is between 1 and 95% by weight, preferably between 10 and 80% by weight.

In addition, the active substance formulations mentioned contain, if appropriate, the adhesives, wetting agents, dispersing agents, emulsifiers, penetrants, preservatives, antifreeze agents, solvents, fillers, carriers, colorants, antifoam agents, evaporation inhibitors and pH and viscosity regulators. Mixtures or mixed formulations with other active substances, such as, for example, insecticides, acaricides, herbicides, safenets, fertilizers, growth regulators or fungicides, are also possible.

Active substances which can be employed as components in combination with the active substances according to the invention in mixed formulations or in a tank mix are, for example, known active substances as they are described, for example, in Weed Research 26, 441–445 (1986), or "The Pesticide Manual", 9th edition, The British Crop Protection Council, 1990/91, Bracknell , England, and in the references cited therein. The following active substances may be mentioned, for example, as herbicides which are known from the literature and which can be combined with the compounds of the formula (I) (note: either the "common name" as defined by the International Organization for Standardization (ISO) or the chemical name, if appropriate, together with a conventional code number, are given):

acetochlor; acifluorfen; aclonifen; AKH 7088, i.e. [[[1-[5-[2-chloro-4-(trifluoromethyl)-phenoxy]-2-nitrophenyl]-2-methoxyethylidene]-amino]-oxy]acetic acid and its methyl ester; alachlor; alloxydim; ametryne; amidosulfuron; amitrol; AMS, i.e. ammonium sulfamate; anilofos; asulam; atrazin; aziprotryne; barban; BAS 516 H, i.e. 5-fluoro-2-phenyl-4H-3,1-benzoxazine-4-one; benazolin; benfluralin; benfuresate; bensulfuronmethyl; bensulide.; bentazone; benzofenap; benzofluor, benzoylprop-ethyl; benzthiazurone; bialaphos; bifenox; bromacil; bromobutide; bromofenoxim; bromoxynil; bromuron; buminafos; busoxinone; butachlor; butamifos; butenachlor; buthidazole; butralin; butylate; carbetamide; CDAA, i.e. 2-chloro-N,N-di-2-propenylacetamide; acetamide; CDEC, i.e. 2-chloroallyl diethyldithiocarbamate; CGA 184927, i.e. 2-[4-[(5-chloro-3-fluoro-2-pyridinyl)-oxy]-phenoxy]-propanoic acid and its 2-propynyl ester; chlomethoxyfen; chloramben; chlorazifopbutyl, pirifenop-butyl; chlorbromuron; chlorbufam; chlorfenac; chlorflurecol-methyl; chloridazon; chlorimuron-ethyl; chlornitrofen; chlorotoluron; chloroxuron; chlorpropham; chlorsulfuron; chlorthaldimethyl; chlorthiamld; cinmethylin; cinosulfuron; clethodim; clomazone; clomeprop; cloproxydim; clopyralid; cyanazine; cycloate; cycloxydim; cycluron; cyperquat; cyprazine; cyprazole; 2,4-DB; dalapon; desmediphan; desmetryn; di-allate; dicamba; dichlobenil; dichlorlprop; diclofop-methyl; diethatyl; difenoxuron; difenzoquat; diflufenican; dimefuron; dimethachlor; dimethametryne; dimethazone, clomazon; dimethipin; dimetrasulfuron, cinosulfuron; dinitramine; dinoseb; dinoterb; diphenamid; dipropetryn, diquat; dithiopyr; diuron; DNOC; eglinazineethyl; EL 177, i.e. 5-cyano-1-(1,1-dimethylethyl)-N-methyl-3H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]-phenyl]-ethanesulfonamide; F6285, i.e. 1-[5-(N-methylsulfonyl)-amino-2,4-dichorophenyl]-3-methyl-4-difluoromethyl-1,2,4-triazol-5-one; fenoprop; fenoxan, s. clomazon; fenoxaprop-ethyl; fenuron; flamprop-methyl; flazasulfuron; fluazifop and its ester derivatives; fluchoralin; flumetsulam; N-[2,6-difluorophenyl]-5-methyl-(1,2,4)-triazolo[1,5a] pyrimidine-2-sulfonamide; flumeturon; flumipropyne; fluorodifen; fluoroglycofen-ethyl; fluridone; fluorchlo-ridone; fluroxypyr; flurtamone; fomesafen; fosamine; furyloxyfen; glufosinate; glyphosate; halosaten; haloxyfop and its ester derivatives; hexazinone; Hw 52, i.e. N-(2,3-dichlorophenyl)-4-(ethoxymethoxy)-benzamide; imazamethabenz-methyl; imazapyr; imazaquin; imazethamethapyr; imazethapyr; imazosulfuron; ioxynil; isocarbamid; isoropalin; isoproturon; isouron; isoxaben; isoxapyrifop, karbutilate; lactofen; lenacil; linuron; MCPA; MCPB; mecoprop; mefenacet; mefluidid; metamitron; metazachlor; methabenzthiazuron; metham; methazole; methoxyphenone; methyldymron; metobromuron; metolachlor; metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)-phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiazon; oxyfluorfen; paraquat; pebulate; pendimethalin; perfluidone; phenmedipham; phenisopham; phenmedipham; picloram; piperophos; piributicarb; pirifenop-butyl; pretilachlor; primisulfuron-methyl; procyazine; prodiamine, profluralin; proglinazine-ethyl; prometon; prometryne; propachlor; propanil; propaquizafop and its ester derivatives; propazine; propham; propyzamide; prosulfalin; prosulfocarb; prynachlor; pyrazolinate; pyrazon; pyrazosulfuron-ethyl; pyrazoxyfen; pyridate; quinclorac; quinmerac; quinofop and its ester derivatives, quizalofop and its ester derivatives; quizalofopethyl; quizalofop-p-tefuryl; renriduron; dymron; S 275, i.e. 2-[4-chloro-2-fluoro-5-(2-propynyloxy)-phenyl]-4,5,6,7-tetrahydro-2H-indazole; S 482, i.e. 2-[7-fluoro-3,4-dihydro-3-oxo-4-(2-propynyl)-2H-1,4-benzoxazin-6-yl]-4,5,6,7-tetrahydro-1H-isoindole-1,3(2H)-dione; secbumeton; sethoxydim; siduron; simazine; simetryn; SN 106279, i.e. 2-[[7-[2-chloro-4-(trifluoro-methyl) phenoxy]-2-naphthalenyl]-oxy]-propanoic acid and its methyl ester; sulfometuron-methyl; sulfazuron; flazasulfuron; sulfuron; TCA; tebutam; tebuthiuron; terbacil; terbucarb; terbuchlor; terbumeton; terbuthylazine; terbutryne; TFH 450, i.e. N,N-diethyl-3-[(2-ethyl-6-methylphenyl)sulfonyl]-1H-1,2,4-triazole-1-carboxamide; thiazafluron; thifensulfuron-methyl; thiobencarb; tiocarbazil; tralkoxydim; tri-allate; triasulfuron; triazofenamide; tribenuron-methyl; triclopyr; tridiphane; trietazine; trifluralin; trimeturon; vernolate; WL 110547, i.e. 5-phenoxy-1-[3-(trifluoromethyl)-phenyl]-1H-tetrazole.

For use, the formulations, present in commercially available form, are diluted, if appropriate, in a customary manner, for example using water in the case of wettable powders, emulsifiable concentrates, dispersions and water-dispersible granules. Preparations in the form of dusts, granules for broadcasting and for soil application and also sprayable solutions are usually not further diluted with other inert substances before use.

The application rate required for the compounds of the formula (II) varies with the external conditions, such as, inter alia, temperature, humidity, and the nature of the herbicide used. It can vary within wide limits, for example between 0.001 and 10.0 kg/ha or more of active substance; preferably, however, it is between 0.005 and 5 kg/ha.

A. Chemical Examples

Example 1

1a) 2-Benzylmercapto-3-fluoromethylsulfonyleminopyridine

A solution of 6.6 g (0.05 mol) of fluoromethanesulfonyl chloride in 50 ml of dichloromethane is added dropwise at 0° C. to 21.6 g (0.1 mol) of 3-amino-2-benzylmercaptopyridine in 125 ml of dichloromethane, and the mixture is subsequently refluxed for 14 hours. The mixture is cooled, the organic phase is washed 3 times using dilute HCl and once using water and extracted with 2N sodium hydroxide solution, and the sodium hydroxide solution phase is acidified using concentrated HCl to bring the pH to 1 and extracted using dichloromethane. After drying and evaporation, 9.4 g (60% of theory) of 2-benzylmercapto-3-fluoromethylsulfonylaminopyridine of melting point 130°–131° C. remain.

1b) 2-Benzylmercapto-3-(N-fluoromethylsulfonyl-N-methyl-amino)pyridine 10.6 g (0.034 mol) of the compound of Example 1 are refluxed for 10 hours with 4.7 g (0.034 mol) of potassium carbonate and 4.3 g (0.034 mol) of dimethyl sulfate in 300 ml of acetone. The mixture is cooled, the solvent is removed, the residue is taken up in 200 ml of dichloromethane, and the organic phase is washed with 200 ml of water, dried and evaporated. 11.1 g (100% of theory) of 2-benzylmercapto-3-(N-fluoromethylsulfonyl-N-methyl-amino)pyridine are obtained; NMR (CDCl$_3$): δ (ppm)=3.22 (s, 3H; N—CH$_3$); 4.48 (s, 2H, S—CH$_2$), 5.18 (d.J=46 Hz, 2H, CH$_2$F), 7.07 (dd, 1H, pyridine-H5), 7.17–7.45 (m, 5H; phenyl), 7.56 (dd, 1H; pyridine-H4), 8.45 (dd, 1H; pyridine-H6).

1c) 3-(N-fluoromethylsulfonyl-N-methylamino)-2-pyridine sulfonamide

Approximately 21 g (0.3 mol) of chlorine are passed, at 0° C., into a solution of 5.0 g (0.015 mol) of the compound of Example 2 in 40 ml of dichloromethane and 40 ml of water. The mixture is stirred at this temperature for approximately 15 minutes, and a vigorous stream of nitrogen is subsequently passed into the solution for 15 minutes. The phases are separated, and the organic phase is washed with water and dried. The product is cooled to −70° C., and ammonia is passed in until the solution gives an alkaline reaction. The mixture is allowed to come to room temperature, 50 ml of water are added, and the organic phase is separated off, dried and evaporated. After trituration of the residue with diethyl ether, filtration and drying, 3.4 g (78% of theory) of 3-(N-fluoromethylsulfonyl-N-methylamino)-2-pyridinesulfonamide of melting point 160°–162° C. are obtained.

1d) 3-(4,6-dimethoxypyrimidine-2-yl)-1-[3-(N-fluoromethylsulfonyl-N-methylamino)-2-pyridylsulfonyl)urea (Compound No. 1 of Table 1)

1.0 g (6.6 mmol) of 1,5-diazabicyclo[5.4.0]-undec-5-ene is added to a solution of 1.5 g (5.3 mmol) of the compound of Example 3 and 1.75 g (6.4 mmol) of phenyl-N-(4,6-dimethoxypyrimidine-2-yl)carbamate in 20 ml of acetonitrile, and the mixture is stirred for 24 hours at room temperature. It is poured into 50 ml of water, and the mixture is acidified using 2N hydrochloric acid and extracted 3 times using dichloromethane. Drying and evaporation is followed by trituration of the residue with diethyl ether. 2.3 g (94% of theory) of 3-(4,6-dimethoxypyrimidine-2-yl)-1-[3-(N-fluoromethylsulfonyl-N-methylamino)-2-pyridylsulfonyl) urea of m.p. 181°–183° C. (decomposition) are obtained.

The compounds of the formula (II) of Table 1 below are obtained by, or in analogy to, the processes of Examples 1a–1d.

TABLE 1

Examples of compounds of the formula (II)

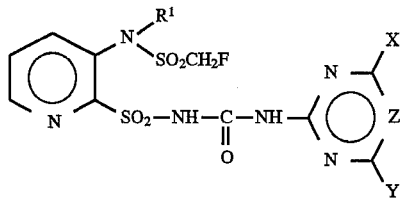

| Comp. No. | R$^1$ | X | Y | Z | m.p. [°C.] |
|---|---|---|---|---|---|
| 1 | CH$_3$ | OCH$_3$ | OCH$_3$ | CH | 175–178 (decomp.) |
| 2 | CH$_3$ | OCH$_3$ | CH$_3$ | CH | |
| 3 | CH$_3$ | CH$_3$ | CH$_3$ | CH | |
| 4 | CH$_3$ | OCH$_3$ | OCH$_3$ | N | |
| 5 | CH$_3$ | OCH$_3$ | CH$_3$ | N | |
| 6 | CH$_3$ | CH$_3$ | CH$_3$ | N | |
| 7 | CH$_3$ | Cl | OCH$_3$ | CH | |
| 8 | CH$_3$ | OCHF$_2$ | OCHF$_2$ | CH | |
| 9 | CH$_3$ | OCH$_3$ | OC$_2$H$_5$ | CH | |
| 10 | CH$_3$ | CF$_3$ | OCH$_3$ | CH | |
| 11 | CH$_3$ | OCH$_3$ | C$_2$H$_5$ | CH | |
| 12 | CH$_3$ | OCHF$_2$ | CH$_3$ | CH | |
| 13 | C$_2$H$_5$ | OCH$_3$ | OCH$_3$ | CH | |
| 14 | C$_2$H$_5$ | OCH$_3$ | CH$_3$ | CH | |
| 15 | C$_2$H$_5$ | OCH$_3$ | OCH$_3$ | N | |
| 16 | C$_2$H$_5$ | OCH$_3$ | CH$_3$ | N | |
| 17 | C$_2$H$_5$ | OCH$_3$ | OC$_2$H$_5$ | CH | |
| 18 | C$_2$H$_5$ | OCHF$_2$ | OCHF$_2$ | CH | |
| 19 | H | OCH$_3$ | OCH$_3$ | CH | |
| 20 | H | OCH$_3$ | CH$_3$ | CH | |
| 21 | H | CH$_3$ | CH$_3$ | CH | |
| 22 | H | OCH$_3$ | OCH$_3$ | N | |
| 23 | H | OCH$_3$ | CH$_3$ | N | |
| 24 | H | CH$_3$ | CH$_3$ | N | |

Abbreviations:
Comp. No. = Compound No.
m.p. = Melting point
(decomp.) = with decomposition B. Formulation Examples a) A dust is obtained by mixing 10 parts by weight of a compound of the formula (II) and 90 parts by weight of talc as inert substance and comminuting the mixture in a hammer mill.

b) A wettable powder which is readily dispersible in water is obtained by mixing 25 parts by weight of a compound of the formula (II), 64 parts by weight of kaolin-containing quartz as inert substance, 10 parts by weight of potassium ligninsulfonate and 1 part by weight of sodium oleoylmethyltaurinate as wetting and dispersing agent, and grinding the mixture in a pinned disk mill.

c) A dispersion concentrate which is readily dispersible in water is obtained by mixing 20 parts by weight of a compound of the formula (II) with 6 parts by weight of alkylphenlpolyglycol ether (®Triton X 207), 3 parts by weight of isotridecanol polyglycol ether (8 EO) and 71 parts by weight of paraffinic mineral oil (boiling range for example, approximately 255 to above 277° C.), and grinding the mixture in a ball mill to a fineness of below 5 microns.

d) An emulsifiable concentrate is obtained from 15 parts by weight of a compound of the formula (II), 75 parts by weight of cyclohexanone as the solvent and 10 parts by weight of oxethylated nonylphenol as the emulsifier.

e) Water-dispersible granules are obtained by mixing 75 parts by weight of a compound of the formula (II),
10 parts by weight of calcium ligninsulfonate,
5 parts by weight of sodium lauryl sulfate,
3 parts by weight of polyvinyl alcohol and
7 parts by weight of kaolin, grinding the mixture in a pinned disk mill and granulating the powder in a fluidized bed by spraying on water as the granulation liquid.

f) Water-dispersible granules are also obtained by homogenizing and precomminuting, on a colloid mill,
25 parts by weight of a compound of the formula (II),
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water, subsequently grinding the mixture on a bead mill and atomizing and drying the resulting suspension in a spray tower by means of a single-substance nozzle.

g) Extruder granules are obtained by mixing 20 parts by weight of active substance of formula (II), 3 parts by weight of sodium ligninsulfonate, 1 part by weight of carboxymethylcellulose and 76 parts by weight of kaolin, and moistening the mixture with water. This mixture is extruded and subsequently dried in a stream of air.

C. Biological Examples

1. Pre-emergence effect on weeds

Seeds or rhizome pieces of monocotyledon and dicotyledon weed plants were placed in sandy loam soil in plastic pots and covered with soil. The compounds of the formula (II) according to the invention which were formulated in the form of wettable powders or emulsion concentrates were then applied to the surface of the soil cover in the form of aqueous suspensions or emulsions at an application rate of 600 to 800 l of water/ha (converted), in various dosages.

After the treatment, the pots were placed in a greenhouse and kept under good growth conditions for the weeds. After the test plants had emerged, the damage to the plants or the negative effect on the emergence was scored visually after a test period of 3 to 4 weeks by comparison with untreated controls. As shown by the score figures, the compounds according to the invention have a good herbicidal pre-emergence activity against a broad range of grass weeds and dicotyledon weeds. In comparison with the compound of the formula (VI),

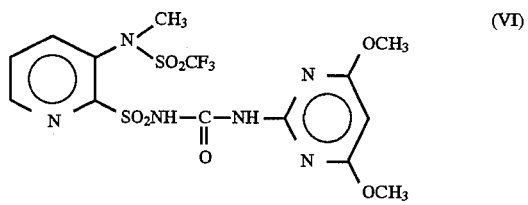

which has a similar structure, Compound No. 1 (Table 1) proved to be truly superior with regard to the herbicidal activity against important harmful plants. The compound of the formula (VI) is disclosed in WO 91/10660 (Comp. No. 840) and EP 451 468 (Example No. 14).

2. Post-emergence effect on weeds

Seeds or rhizome pieces of monocotyledon and dicotyledon weeds were placed in sandy loam soil in plastic pots, covered with soil and grown in a greenhouse under good growth conditions. Three weeks after sowing, the test plants were treated in the three-leaf stage.

The compounds of the formula (II) according to the invention which were formulated as wettable powders or as emulsion concentrates were sprayed in various dosages on the green parts of the plants at an application rate of 600 to 800 l of water/ha (converted) and, after the test plants had remained in the greenhouse for about 3 to 4 weeks under ideal growth conditions, the effect of the preparations was scored visually by comparison with untreated controls.

The agents according to the invention also have a good herbicidal post-emergence action against a broad range of economically important grass weeds and dicotyledon weeds. In comparison with the compound of the formula (VI) (see the previous Section 1), Comp. No. 1 of Table 1 also shows a clear superiority with regard to the herbicidal activity against important harmful plants when used post-emergence.

3. Tolerance by crop plants

In further greenhouse experiments, seeds of a substantial number of crop plants and weeds were placed in sandy loam soil and covered with soil.

Some of the pots were treated immediately as described under Section 1 (1.), and the remaining pots were placed in a greenhouse until the plants had developed two to three true leaves and then sprayed with various dosages of the substances of the formula (II) according to the invention, as described under 2. Visual scoring four to five weeks after the application and after the plants had been in the greenhouse revealed that the compounds according to the invention did not inflict any damage to dicotyledon crops such as, for example, soya beans, cotton, oilseed rape, sugar beet and potatoes when used pre- and post-emergence, even when high dosages of active substance were used. Moreover, some substances also left Gramineae crops such as, for example, barley, wheat, rye, Sorghum species, maize or rice unharmed. The compounds of the formula (II) therefore have a high selectivity when used for controlling undesired plant growth in agricultural crops.

We claim:

1. A compound of the formula (II) or a salt thereof,

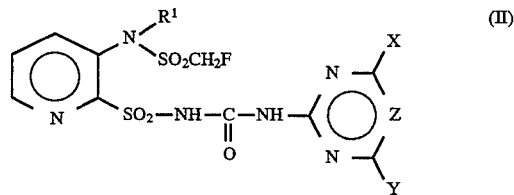

in which

R¹ is hydrogen, methyl or ethyl,

Z is CH and one of the radicals X and Y is halogen, $(C_1-C_2)$alkyl, $(C_1-C_2)$alkoxy, $OCHF_2$ or $CF_3$ and the other one of the radicals X and Y is $(C_1-C_2)$alkyl, $(C_1-C_2)$alkoxy or $OCHF_2$.

2. A compound of the formula (II) or a salt thereof as claimed in claim 1, wherein X and Y independently of one another are methoxy, ethoxy, difluoromethoxy or methyl.

3. A compound of the formula (I) or a salt thereof as claimed in claim 1 wherein:

R¹ is hydrogen or methyl,

X is methoxy or methyl, and is methoxy or methyl.

4. A compound of the formula (I) or a salt thereof as claimed in claim 3 wherein R¹ is hydrogen.

5. A compound of the formula (I) or a salt thereof as claimed in claim 3 wherein R¹ is methyl.

6. A method of controlling harmful plants wherein an effective amount of a compound of the formula (II) or a salt thereof as claimed in claim 1 is used as a herbicide.

7. A herbicide or plant growth regulator composition which comprises a compound of the formula (II) or a salt thereof as claimed in claim 1 and customary formulation auxiliaries.

8. A method for regulating growth of plants, which comprises applying a plant-growth-regulatory active amount of one or more compounds of the formula (II) as claimed in claim 1 to the plant or the area containing the plants or their seeds.

* * * * *